(12) United States Patent
Pfeiffer et al.

(10) Patent No.: US 6,200,301 B1
(45) Date of Patent: Mar. 13, 2001

(54) PROCESS AND DEVICES FOR DETERMINING THE INSTANT OF INJECTION AND THE DURATION OF INJECTION IN THERMODILUTION MEASUREMENTS

(75) Inventors: Ulrich Pfeiffer; Stefan Joeken; U. Seebauer, all of München (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/144,276

(22) Filed: Aug. 31, 1998

(30) Foreign Application Priority Data

Sep. 5, 1997 (DE) .............................................. 197 38 942

(51) Int. Cl.[7] .................................................. A61M 31/00
(52) U.S. Cl. .............................................................. 604/503
(58) Field of Search ............................ 604/503, 66, 20; 128/640, 691–692; 606/32

(56) References Cited

U.S. PATENT DOCUMENTS

| 3,915,155 | 10/1975 | Jacobson et al. |  |
|---|---|---|---|
| 4,476,877 | 10/1984 | Barker . |  |
| 4,730,623 | 3/1988 | Lee . |  |
| 4,901,734 | * | 2/1990 | Griffin et al. ........................ 128/692 |
| 5,520,180 | * | 5/1996 | Uy et al. ............................. 128/640 |
| 5,526,817 | * | 6/1996 | Pfeiffer et al. ....................... 128/691 |

FOREIGN PATENT DOCUMENTS

| 0 177 353 | 9/1984 | (EP) . |
| 64-56032 | 3/1989 | (JP) . |
| 3-503731 | 8/1991 | (JP) . |
| WO 94/20017 | 9/1994 | (WO) . |

* cited by examiner

Primary Examiner—Sharon Kennedy
Assistant Examiner—Kevin C. Sirmons
(74) Attorney, Agent, or Firm—Nixon Peabody LLP; Donald R. Studebaker

(57) ABSTRACT

The present invention relates to a process and devices for determining the instant of injection and the duration of injection in thermodilution measurements in which an injectate fluid at a temperature deviating from the temperature of the blood of a patient is injected at a specific injection site into a blood vessel of the patient and the temperature of the blood is measured at a measuring site downstream of the injection site, the injectate fluid being used at approximately room temperature and, before entry into the blood vessel, passed by a temperature sensor which, before the measurement, has a temperature deviating from room temperature, the temperature determined by the temperature sensor being sensed continuously, the instant of the beginning of injection being determined from a change occurring in the sensed temperature and the instant of the end of injection being determined from a subsequently occurring change in direction of the temperature profile.

7 Claims, 3 Drawing Sheets

Injection curve profile with the new sensor system

Injection curve profile with conventional systems

Injection curve profile with the new sensor system

Flowchart for calculating the instant of injection, its duration and temperature.

PROCESS AND DEVICES FOR DETERMINING THE INSTANT OF INJECTION AND THE DURATION OF INJECTION IN THERMODILUTION MEASUREMENTS

BACKGROUND OF THE INVENTION

1. Field of the Invention

The present invention relates to a process and devices for detecting the instant of injection and for determining the duration of injection in hemodynamic monitoring by means of thermodilution.

2. Description of the Prior Art

The measurement of hemodynamic parameters, for example the cardiac output, is largely performed at present either by means of pulmonary arterial or transcardiopulmonary thermodilution (Pfeiffer U. J., Knoll R. (1993): Process for Determining a Patient's Circulatory Fill Status. U.S. Pat. No. 5,526,817) or else by means of thermo-dye-dilution (Pfeiffer, U. J., Backus G., Blümel G., Eckart J., Muller P., Winkler P., Zeravik J., Zimmermann G. J. (1990): A Fiberoptics-Based System for Integrated Monitoring of Cardiac Output, Intrathoracic Blood Volume. Extravascular Lung Water, $O_2$ Saturation, and a–v Differences. Practical Applications of Fiberoptics in Critical Care Monitoring, Springer Verlag, 114–125). In these processes, a defined volume of an indicator substance which is as cold as possible, for example glucose or saline solution, is injected. The instant of injection into the body is registered by means of an extracorporeal temperature sensor which is integrated directly in the injection lumen.

At the same time, the thermodilution measurement is started by means of a thermosensor, which in the case of pulmonary arterial measurement is located in the distal lumen of the pulmonary artery catheter in the Arteria pulmonalis or, in the case of transcardiopulmonary measurement, in the tip of a catheter lying in the Arteria femoralis or in the Aorta abdominalis. By plotting the thermodilution curve, the cardiac output can be calculated, for example by means of the Stewart-Hamilton method.

The special aspect of the transcardiopulmonary method is the additional determination of a number of cardiovascular parameters, in particular for assessing the output status, for example by the intrathoracic blood volume. For the calculation of these parameters, knowledge of the characteristic times of the indicators, in particular the mean transit time and exponential fall time, is required. To be able to calculate these exactly, the instant of injection, the mean passage time of the injectate and the duration of injection must in turn be accurately measured, which is accomplished by means of the curve plotted using the extracorporeal temperature sensor (cf. FIG. 1, which reproduces the injection curve profile with a known injectate temperature sensor system; in contrast to this, FIG. 2 shows the injection curve profile with a sensor system according to the invention set out below).

As a function of the temperature difference between ambient air and injectate, the value $T_{inj}$, required for correct measurements, is calculated using additionally determined correction factors.

A major disadvantage of the existing technique is that injectate of a temperature deviating from room temperature was required for optimum measurements in order to determine exactly the instant of injection and the duration of injection, since the volume in the customary extracorporeal injectate temperature sensor housing is essentially at room temperature. To be able to detect the instant at which injection starts and to be able to calculate the duration of injection from the temperature profile, a clear temperature difference between the fluid at the sensor before injection and the injectate is required.

For this reason, it must be ensured that the injection solution is available in a well cooled state at any time. This means additional work also for the nursing staff in intensive care units and in operating rooms. In addition, measurements often do not proceed absolutely smoothly, with the result that injectate taken out of cooling too early may already have warmed up again by the time it is used; the same problem arises if a number of measurements are carried out at short intervals one after the other.

The use of cooling sets, which can be installed at the patient's bed, does offer the advantage of an injectate cooled for a certain time directly at the patient, but again brings about considerable disadvantages due to increased work, for example to obtain fresh ice for the cooling box, and due to the costs additionally incurred.

SUMMARY OF THE INVENTION

Proceeding from the abovementioned disadvantages and shortcomings of the prior art, the present invention is based on the object of providing a process for detecting the instant of injection and for determining the duration of injection which allows optimum hemodynamic measurements with injectate kept at room temperature by means of the thermodilution technique, it being intended that the process can be accomplished without more work and without any particular additional costs.

This object is achieved by a process for determining the instant of injection and the duration of injection in thermodilution measurements in which an injectate fluid at a temperature deviating from the temperature of the blood of a patient is injected at a specific injection site into a blood vessel of the patient and the temperature of the blood is measured at a measuring site downstream of the injection site, the injectate fluid being used at approximately room temperature and, before entry into the blood vessel, passed by a temperature sensor which, before the measurement, has a temperature deviating from room temperature, the temperature determined by the temperature sensor being sensed continuously, the instant of the beginning of injection being determined from a change occurring the sensed temperature and the instant of the end of injection being determined from a subsequently occurring in change in direction of the temperature profile.

U.S. Pat. No. 4,901,734 discloses a known pulmonary artery catheter. Such a pulmonary artery catheter is advanced via the Vena cava superior, the central vein, the right-hand atrium and the right-hand ventricle into the Arteria pulmonalis. For this reason, the pulmonary artery catheter has a proximal lateral opening, which with the positioning described above lies in the central vein, while the distal sensor, provided in the region of the tip, lies—as mentioned—in the Arteria pulmonalis.

The catheter device known from U.S. Pat. No. 4,901,734 is formed with a number of lumens and has a distally arranged thermistor, a proximally arranged thermistor and a plurality of electrical sensor means connected to the thermistors. In this case, the proximal thermistor is arranged such that it is essentially immersed totally in the blood/injectate mixture in order to immediately determine its temperature.

However, there is a considerable disadvantage to be seen in the fact that the temperature sensor is provided in the form of the proximal thermistor directly in the injection lumen, to the extent that as a result the injectate flow must to a certain extent be "diverted", that is to say must be directed around the temperature sensor and, as it does so, mixes directly with the blood flowing past the proximal lateral opening due to turbulence. Owing to the turbulence described, the exact determination of the temperature of the injectate, and consequently also the precise determination of the instant at which the injectate arrives, is not possible, in particular if there is a comparatively small difference between the temperature of the injectate and the temperature of the blood. In addition, such a diversion of the injectate flow is not only troublesome but, with certain catheter positions, may also hinder and/or delay the introduction of the injectate.

Furthermore, in the case of the pulmonary artery catheter known from U.S. Pat. No. 4,901,734, no possibility is provided for determining the instant of injection and the duration of injection. The sensing of the temperature of the blood/injectate mixture serves in particular for determining the so-called "temperature base line".

The shortened response time aimed for according to U.S. Pat. No. 4,901,734, of 0.5 to 0.75 seconds, has the effect that the temperature base line is reached more quickly and its determination is more exact. However, a time measurement is neither provided nor intended.

Proceeding from the abovementioned disadvantages and shortcomings of the prior art according to U.S. Pat. No. 4,901,734, the present invention is based on the object of providing a central vein catheter for detecting the instant of injection and for determining the duration of injection which allows optimum hemodynamic measurements with injectate kept at room temperature by means of the thermodilution technique, it being intended that the catheter can be installed without more work and without particular additional costs.

This object is achieved by a central vein catheter for the injection of an injectate fluid having a temperature deviating from the temperature of the blood of the patient into the central vein of the patient for carrying out thermodilution measurements in which the temperature of the blood is measured at a measuring site downstream of the central vein by a separate device, which catheter has:

an elongate catheter body, having at least one injection lumen, with a distal end and a proximal end;

at least one connection device at the proximal end for connecting at least one injectate source to the injection lumen for introducing the injectate fluid;

at least one port of the injectate lumen in the vicinity of the distal end of the catheter body for introducing the injectate fluid into the central vein of the patient;

at least one temperature sensor, which is arranged inside the catheter body upstream of the port of the injection lumen for continuously sensing the temperature of the injection lumen and the connection lines of which are led to a connecting device at the proximal end of the catheter body; and at least one evaluation circuit, which can be connected to the connecting device, for sensing and evaluating the temperature profile determined by the temperature sensor for determining the instant of injection and the duration of injection.

The catheter according to the present invention consequently has at least one injection lumen for the application of medicaments, for parenteral feeding, for removing blood or for measuring the pressure in the central vein. At least one temperature sensor is arranged inside the catheter body upstream of the port of the injection lumen for continuously sensing the temperature of the injection lumen and lies close to the injection lumen, with the result that the temperature sensor, due to its central position, is influenced only relatively little by external factors, for example by disturbing injections through another lumen. An intravasal determination of the injection temperature for the thermodilution is made possible by the abovementioned arrangement.

Since the intravasal dead space in the injection lumen of the catheter is close to body temperature of 37 degrees Celsius, an injectate kept at room temperature of about 20 degrees Celsius is easily detected, because the temperature sensor has a temperature deviating from room temperature during the measurement. Consequently, the instant of injection and the duration of injection can be determined exactly and, in combination with the indicator dilution curves, the passage times of the indicators can be calculated at the measuring sites in the Arteria femoralis/Arteria radialis and also in the Arteria pulmonalis.

In contrast to the prior art according to U.S. Pat. No. 4,901,347, in the case of the central vein catheter according to the invention the injectate flow does not have to be diverted, that is to say it does not have to be directed around the temperature sensor; rather, the temperature determination takes place by it being possible for the injectate to be passed through the injection lumen immediately and by a direct path past the temperature sensor, the injectate is thus not being hindered or delayed in its flow. Consequently, the temperature of the pure injectate and not—as in the case of U.S. Pat. No. 4,901,734—the temperature of the blood/injectate mixture is determined.

In accordance with a preferred embodiment of the present invention the temperature sensor is arranged laterally adjacent to the injection lumen, in order to make possible good thermal contact between the injection lumen and the temperature sensor.

According to a further preferred development, there is provided a further lumen, which is designed as a sensor lumen and in which the temperature sensor is arranged. This further lumen, the so-called sensor lumen, may lie in the direct proximity of the injection lumen opening out at the tip of the catheter device and, due to its central position, is influenced only relatively little by external factors, for example by disturbing injections through another lumen. In this sensor lumen there may be disposed the temperature sensor which makes possible an intravascal determination of the injection temperature for the thermodilution.

U.S. Pat. No. 4,476,877 discloses a device for determining the temperature of an injectate which has an extracorporeal, small-volume sensor housing with a temperature sensor device which is arranged inside the sensor housing and is connected via a line to a measuring computer. The sensor housing is designed at the ends such that it can be connected to the injection lumen of a catheter and, at the opposite end, to an injection system.

However, a considerable disadvantage can be seen in the fact that, in the case of the device known from U.S. Pat. No. 4,476,877, no means are provided for arranging it directly on the skin of a patient and in this way heating up the sensor housing to body temperature of 37 degrees Celsius, to the extent that as a result there it is not possible to use injectate kept at room temperature in combination with the temperature sensor device. Consequently, the device known from U.S. Pat. No. 4,476,877 cannot have a temperature deviating significantly from the room temperature of the injectate during the measurement, as a result of which accuracy and reliability are not ensured in the determination of the duration of injection and the instant of injection.

Proceeding from the abovementioned disadvantages and shortcomings of the prior art according to U.S. Pat. No. 4,476,877, the present invention is based on the object of providing a device for detecting the instant of injection and for determining the duration of injection which allows optimum hemodynamic measurements with injectate kept at room temperature by means of the thermodilution technique, it being intended that the device can be installed without more work and without particular additional costs.

This object is achieved by a device for determining the instant of injection and the duration of injection in thermodilution measurements in which an injectate fluid at a temperature deviating from the temperature of the blood of a patient is injected at a specific injection site into a blood vessel of the patient and the temperature of the blood is measured at a measuring site downstream of the injection site, which device has:

- an extracorporeal sensor housing which has at least one input connection, which can be connected to at least one injectate source, and at least one output connection, which can be connected to a blood vessel catheter;
- at least one temperature sensor which is arranged in the sensor housing, continuously senses the temperature in a region between the input connection and the output connection and can be connected via at least one line to at least one measuring computer; and
- at least one heat contact plate of skin-compatible, heat-conducting material for fastening on the skin of the patient.

The device according to the present invention consequently has an extracorporeal sensor housing and at least one temperature sensor which is arranged in the sensor housing and protrudes into the lumen of the sensor housing. The picked-off temperature signal is passed on to the measuring computer via a line with a suitable connector.

According to the invention, the device has at least one heat contact plate of skin-compatible, heat-conducting material for fastening on the skin of the patient. In this way, the injectate is warmed up in the sensor housing by means of the body heat given off by the patient, to be precise distinctly above room temperature, depending on the skin temperature, the fastening site and the spatial conditions (according to experience with normothermic patients by distinctly more than 2 degrees Celsius).

Consequently, in spite of extracorporeal or extravasal localization of the temperature sensor, there occurs a distinct temperature difference between the injectate at room temperature and the dead space, with the result that an exact and reliable detection of the duration of injection and the instant of injection is in any case ensured.

In contrast to the prior art according to U.S. Pat. No. 4,476,877, in the case of the device according to the present invention there is consequently the possibility of using injectate kept at room temperature in combination with the temperature sensor. Consequently, the device according to the present invention may have a temperature deviating from the room temperature of the injectate during the measurement, as a result of which accuracy and reliability are ensured in the determination of the duration of injection and the instant of injection.

Further developments, features and advantages of the present invention are explained in more detail below with reference to the two exemplary embodiments illustrated by way of example in FIGS. 3 to 5.

BRIEF DESCRIPTION OF THE DRAWINGS

FIG. 3b shows a diagrammatic cross-sectional view of the central vein catheter from FIG. 3a;

DETAILED DESCRIPTION

Figure 1:
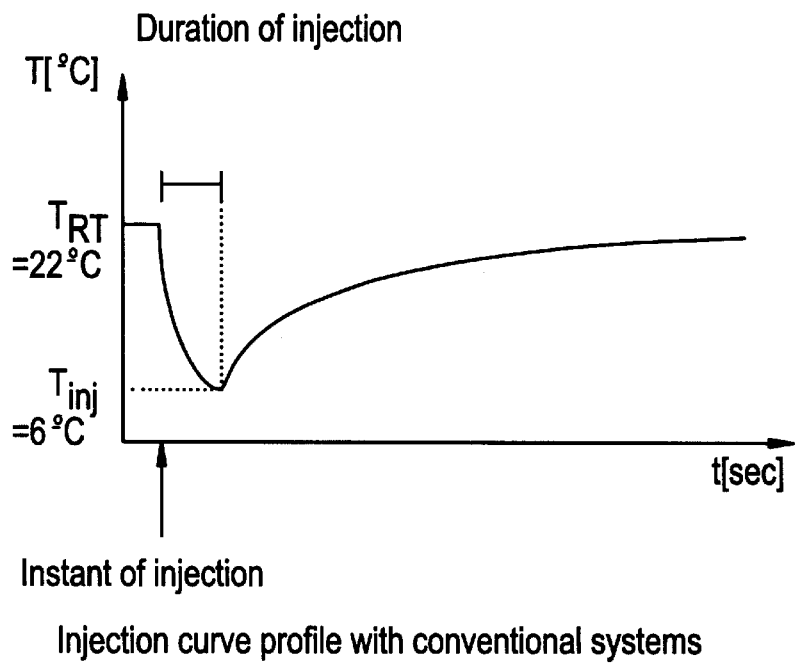
FIG. 1 shows the injection curve profile with an injectate temperature sensor system known from the prior art.
Figure 2:
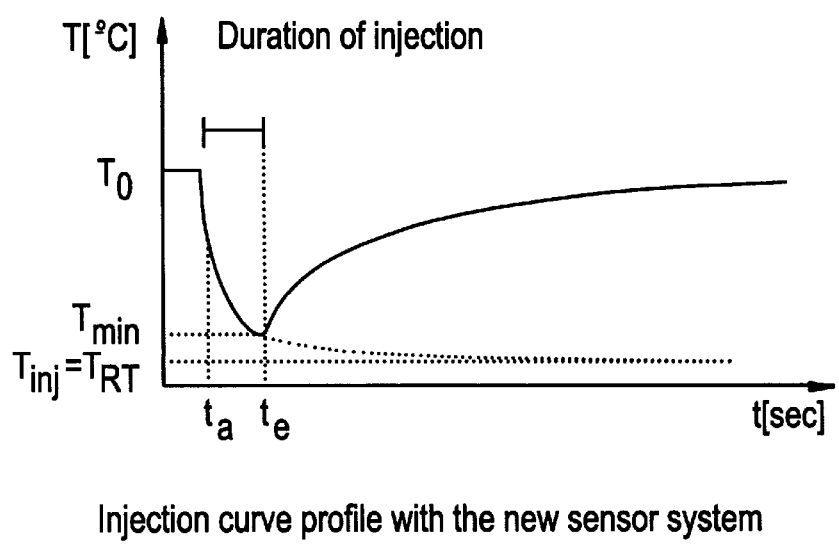
FIG. 2 shows the injection curve profile with a sensor system according to the present invention.
Figure 3A:
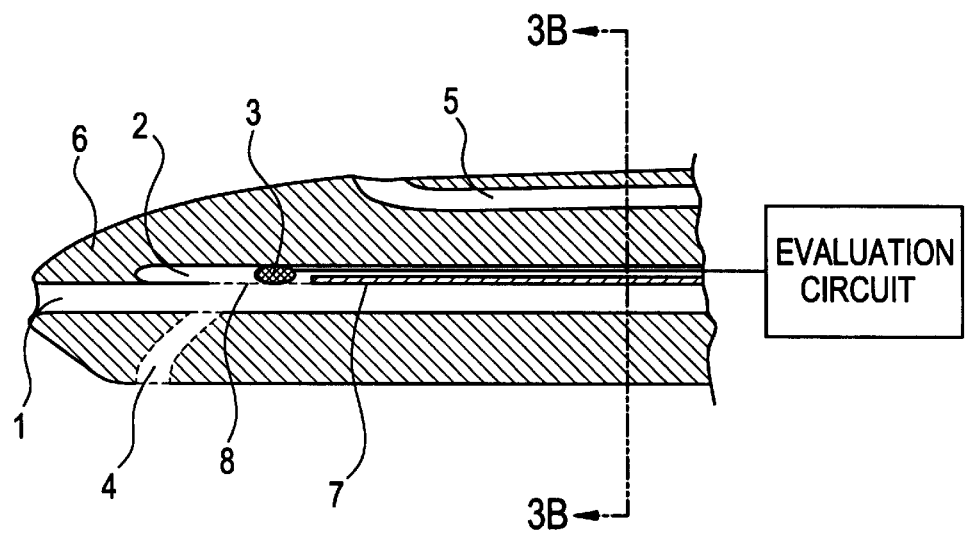
FIG. 3a shows a longitudinal cross sectional view of a central vein catheter according to the present invention.
Figure 3B:
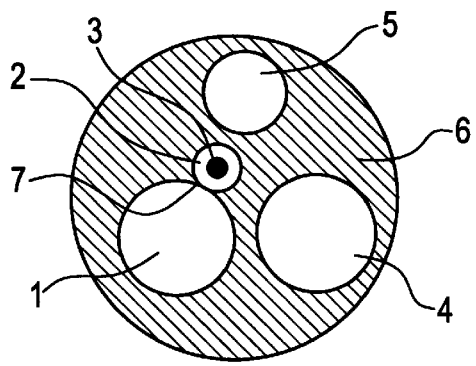
Figure 4:
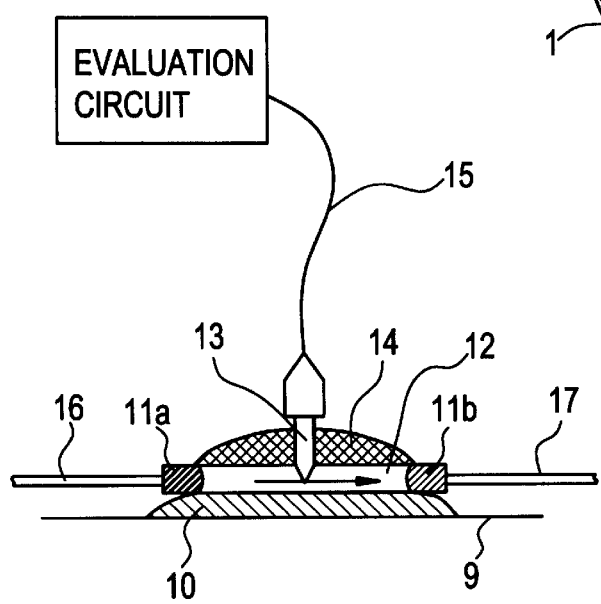
FIG. 4 shows a diagrammatic longitudinal cross sectional view of a device for determining the instant of injection and the duration of injection in thermodilution measurements according to the present invention.

The devices illustrated by way of example in FIGS. 3 and 4 are generally used in a process for determining the instant of injection and the duration of injection in thermodilution measurements in which an injectate fluid at a temperature deviating from the temperature of the blood of a patient is injected at a specific injection site into the blood vessel of the patient and the temperature of the blood is measured at a measuring site downstream of the injection site.

It can be regarded here as a notable special aspect that the injectate fluid is used at approximately room temperature and, before entry into the blood vessel, is passed by a temperature sensor which, before the measurement, has a temperature deviating significantly from room temperature, that is to say by at least two degrees Celsius, the temperature determined by the temperature sensor being continuously sensed, the instant of the beginning of injection being determined from a change occurring in the temperature sensed and the instant of the end of injection being determined from a subsequently occurring change in direction of the temperature profile.

The two exemplary embodiments explained in FIGS. 3 and 4 have in common that the temperature sensor is brought to a temperature deviating from room temperature by contact with the body of the patient. Here, as described in detail below, the temperature sensor in the case of the exemplary embodiment according to FIG. 3 is brought to a temperature deviating from room temperature by blood contact, whereas the temperature sensor in the case of the exemplary embodiment according to FIG. 4 is brought to a temperature deviating from room temperature by outer skin contact.

FIG. 3a shows a diagrammatic longitudinal cross sectional view, FIG. 3b a diagrammatic cross-sectional view of a central vein catheter according to the present invention.

The central vein catheter has a four-lumen catheter body 6, which is ideally produced from not very thrombogenic material, such as for instance polyurethane.

In addition to three conventional lumens 1, 4, 5, with different diameters and ending at the catheter tip or proximally with respect thereto, for the application of medicaments, for parenteral feeding, for removing blood or for measuring the pressure in the central vein, there is centrally in the catheter body 6 a further lumen 2, which as a sensor lumen 2 lies in the direct proximity of the injection lumen 1, opening out at the catheter tip, and, due to its central position, is influenced little by external factors, for example by disturbing injections through one of the other lumens 4, 5.

The sensor lumen 2 ends blind before the catheter tip. In the sensor lumen 2 there is disposed a temperature sensor 3, which at the proximal end of the intravasal catheter portion goes over into a channel extension with a temperature sensor connector (not explicitly shown in FIGS. 3a and 3b). By means of this temperature sensor 3, it is possible to determine intravasally the injection temperature for the thermodilution.

The optimum temperature transfer from the injection lumen 1 to the temperature sensor 3 takes place by means of a very thin separating wall 7 with good heat-conducting properties and by means of a clearance 8 between the injection lumen 1 and the sensor lumen 2.

Since the intravasal dead space in the injection lumen 1 of the catheter is close to body temperature of 37 degrees Celsius, an injection bolus kept at room temperature of about 20 degrees Celsius is easily detected, which is not ensured in the case of the conventional extracorporeal injectate temperature sensors. Thus, the instant of injection and duration of injection can be determined exactly and, in combination with the indicator dilution curves, the passage times of the indicators can be calculated at the measuring sites in the Arteria femoralis/Arteria radialis and also in the Arteria pulmonalis.

With regard to application, it should be noted that the central vein catheter represented in FIGS. 3a and 3b is placed in the customary way by the Seldinger technique. For carrying out a thermodilution, an artery and/or pulmonary artery measuring catheter with temperature sensor is additionally required. Before the beginning of a measurement, the temperature sensor connector of the central vein catheter is connected to a device processing the associated algorithm (cf. FIG. 5); then the measurements are carried out.

FIG. 4 shows a diagrammatic longitudinal sectional view of a device for determining the instant of injection and the duration of injection in thermodilution measurements according to the present invention. In such thermodilution measurements, an injectate fluid at a temperature deviating from the temperature of the blood of a patient is injected at a specific injection site into a blood vessel of the patient and the temperature of the blood is measured at a measuring site downstream of the injection site.

For this purpose, the device has an extracorporeal, small-volume sensor housing 12 of transparent plastic, which is provided proximally with an input connection in the form of a female Luer lock connection 11a, which can be connected to an injectate source, and distally with an output connection in the form of a male Luer lock connection 11b, which can be connected to a blood vessel catheter.

Recessed centrally into the sensor housing 12 there is a temperature sensor 13, which continuously senses the temperature in a region between the input connection 11a and the output connection 11b and protrudes into the lumen of the sensor housing 12. By means of a suitable connector, the temperature signal picked off here can be passed on via a line 15 to a measuring computer.

The sensor housing 12 is integrated into a heat contact plate 10 of skin-compatible, heat-conducting material, which is designed as an adhesive plate 10 and accordingly can be fastened directly on the skin 9 of the patient.

On the side facing away from the body, the sensor housing 12 is provided toward the ambient air with a heat-insulating layer 14. In this way, the fluid in the sensor housing 12 is warmed up by the heat given off by the patient, to be precise distinctly above room temperature, depending on the skin temperature, fastening site and spatial conditions (for example intensive care unit, operating room), according to experience in the case of normothermic patients by distinctly more than 2 degrees Celsius. Thus, in spite of extracorporeal or extravasal localization of the temperature sensor 13, there occurs a distinct temperature difference between the injectate at room temperature and the dead space, with the result that a reliable detection of the injection is ensured in this case as well.

With regard to the application, it should be noted that, after a central vein or pulmonary artery catheter has been placed by the Seldinger technique, the device represented in FIG. 4 is fitted proximally onto the injection system and distally onto the injection lumen of the central vein or pulmonary artery catheter by means of the Luer lock connections 11a and 11b, respectively, after proper venting. For a transcardiopulmonary thermodilution, the corresponding catheter is placed into the Arteria femoralis/Arteria radialis.

Figure 5:
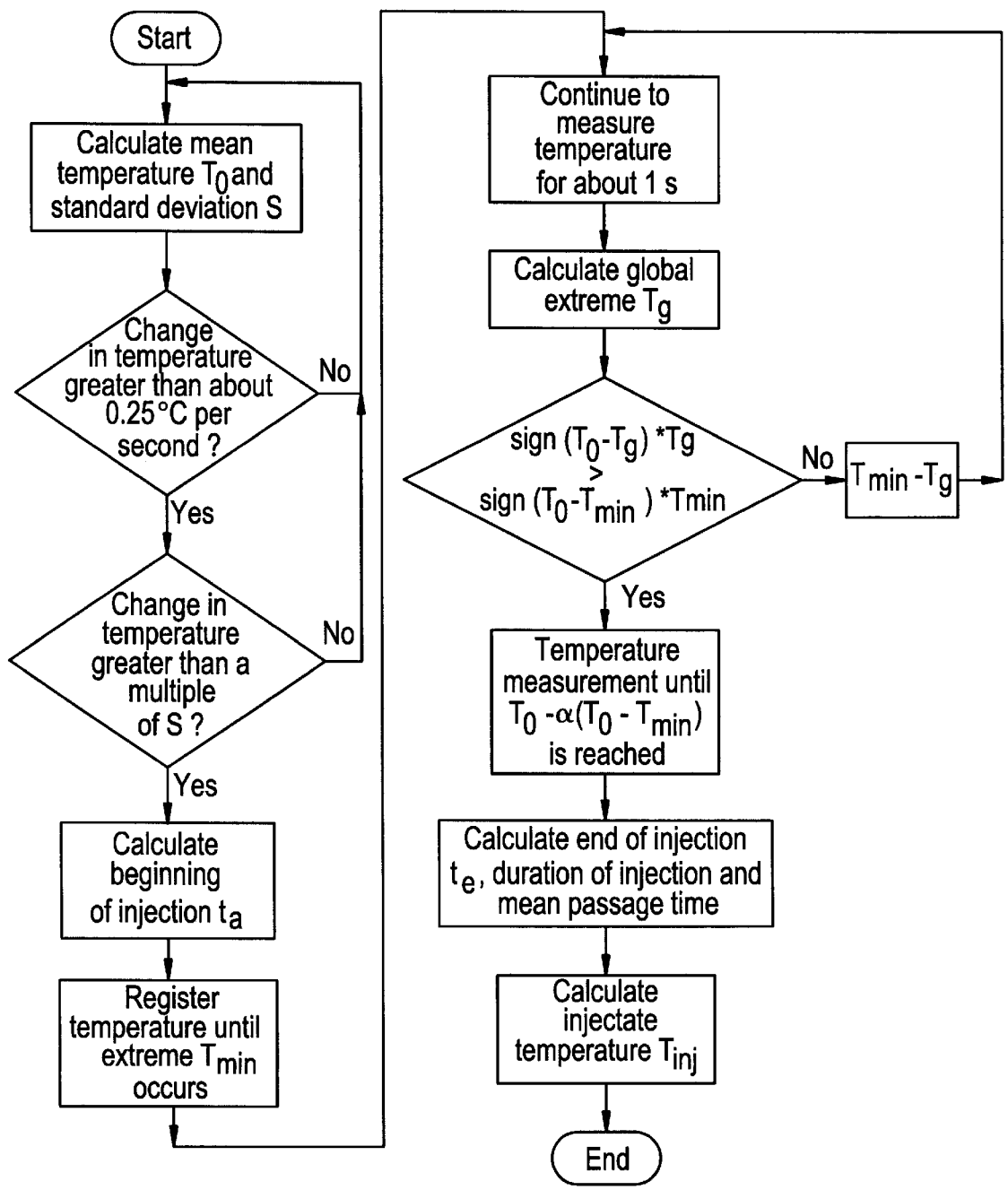
FIG. 5 shows a flowchart for determining the instant of injection, the duration of injection and the temperature.

The line 15 for transferring the temperature signal is fastened by means of a suitable connector on the temperature sensor 13 and is connected to a device processing the corresponding algorithm (cf. FIG. 5). Subsequently, the measurements are carried out.

An exemplary embodiment which is not represented in the figures largely corresponds to the exemplary embodiment according to FIG. 4. In addition, here there is provided a device for the externally activated warming up or cooling of the temperature sensor. This is necessary in situations in which the patient does not provide adequate body heat of his/her own, for example during operations in deep hypothermia. The sensor temperature deviates distinctly from room temperature by means of a control mechanism integrated in the associated device.

The use of the temperature sensors known from the prior art led to the patient being given injectate at three temperatures via the injection lumen of the catheter; these were a) the intracorporeal dead space at body temperature, b) the extracorporeal volume at room temperature and c) the cooled bolus at distinctly less than room temperature. In contrast to this, in the device according to the present invention the extracorporeal volume and the bolus have the same temperature, with the result that overall only two temperatures occur in the essential volumes which contribute to the injected amount of heat. Accordingly, the injected amount of heat can be determined more accurately, with the result that possible error sources of a thermodilution are reduced.

In the exemplary embodiment according to FIG. 4, it can be ignored here that the minimal volume of the sensor housing 12 is warmed slightly with respect to room temperature. As in the other exemplary embodiments as well, the heat source, for example body heat, or the heat sink, is utilized for determining the instant of injection and duration of injection, which takes place with the aid of the following algorithm (cf. FIG. 5):

1. Monitor continuously the temperature at the injectate sensor, which for this purpose is fed into the measuring device, and calculate progressively the mean value $T_0$ and the standard deviation S of the temperature.

2. If the temperature deviates in about one second by more than about 0.25 degree Celsius, but at least by a multiple of the standard deviation S, from the mean value $T_0$, the beginning of injection is detected at this instant $t_a$ and the procedure is continued with step 3. Otherwise, go back to step 1.

3. Continue recording the temperature until it again tends toward the mean value $T_0$. There is subsequently at least one local extreme $T_{min}$ of the injectate temperature.

4. Continue measuring the temperature for a short period of time, for example for one second, and determine the global extreme of the temperature $T_g$ since the beginning of injection, where $\sin(T_0-T_g)=\sin(T_0-T_{min})$. Here, $\sin(x)$ is the sin function with $\sin(x)=1$ for $x>0$ and $\sin(x)=-1$ for $x<0$.

5. If $\sin(T_0-T_g)*T_g$ is less than or equal to $\sin(T_0-T_{min})*T_{min}$, then make $T_{min}=T_g$ and continue with step 4, with the result that short-term fluctuations of the injectate temperature do not disturb the search for the extreme. Otherwise, proceed to step 6.

6. Register the temperature until it again reaches $T_0-\alpha*(T_0-T_{min})$. In this, $\alpha$ lies between zero and one and may either be assumed to be constant or calculated from the standard deviation S.

7. The last recorded temperature data are used to determine the instant $t_e$ since when the temperature has been tending toward $t_0$ in a strictly monotonic function over time. The instant $t_e$ is the sought end of injection, with the result that the duration of injection can be calculated with $t_e-t_a$ and the average injectate passage time can be calculated with $t_a+(t_e-t_a)/2=(t_a+t_e)/2$.

8. Since the minimum temperature $T_{min}$ of the sensor does not exactly reproduce the injectate temperature $T_{inj}$, in particular in the case of injection of short duration, an algebraically or exponentially falling function, for instance $T_{inj}+(T_0-T_{inj})*\exp(-(t-t_a)/\tau)$, can be made to fit the injection curve for times t from the interval $[t_a, t_e]$, by determining the parameters $T_{inj}$ and $\tau$. If, for example to save computing time, no fit is carried out, to simplify matters $T_{inj}=T_{min}$ is set.

With the aid of the computing specification given in steps 1 to 8, the variables sought, instant of injection, duration of injection and injectate temperature, are determined simultaneously with the data acquisition. However, while maintaining the essential computing steps, the algorithm may also be modified such that the injection parameters sought are determined only after the temperature measurement. The procedure may also be extended such that the duration of injection must not exceed a predetermined time period, for example of six seconds, and accordingly the algorithm, in particular steps 4 and 5, cannot be endlessly repeated and a termination can be ensured.

All the systems illustrated in the exemplary embodiments, that it to say both the intravasal injectate temperature sensor integrated in the catheter and the heat-insulated extracorporeal injectate temperature sensor housing, with or without external heat source or heat sink, ensure a reliable detection and determination of the instant of injection and the duration of injection in measurements of the hemodynamics with injectate kept at room temperature. In this way, the measuring procedure is facilitated, the costs, for example for expensive cooling sets, are lowered and the attentiveness of the physician to the patient is not adversely affected.

What is claimed is:

1. A process for determining an instant of injection and a duration of injection in thermodilution measurements, the process comprising the steps of:

providing an injectate fluid at a temperature deviating from a temperature of a blood of a patient and having a temperature at approximately room temperature;

providing a temperature sensor having a temperature deviation from room temperature;

injecting said injectate fluid at a specific injection site into a blood vessel of said patient;

passing said injectate fluid over said temperature sensor and reading continuously a temperature sensed by said temperature sensor;

measuring a temperature of the blood at a measuring site downstream of said injection site;

determining an instant of a beginning of injection from a change occurring in said temperature sensed by said temperature sensor; and determining an instant of an end of injection from a subsequently occurring change in direction of said temperature sensed by said temperature sensor.

2. The process as claimed in claim 1, wherein the temperature of the temperature sensor deviates significantly from room temperature.

3. The process as claimed in claim 1, wherein the temperature of the temperature sensor deviates from room temperature by at least two degrees Celsius.

4. The process as claimed in claim 1, wherein the temperature sensor is brought to a temperature deviating from room temperature by supplying heat or by active or passive cooling from outside.

5. The process as claimed in claim 1, wherein the temperature sensor is brought to a temperature deviating from room temperature by contact with the body of the patient.

6. The process as claimed in claim 5, wherein the temperature sensor is brought to a temperature deviating from room temperature by thermal contact with the blood of the patient.

7. The process as claimed in claim 5, wherein the temperature sensor is brought to a temperature deviating from room temperature by thermal contact with the outer skin of the patient.

* * * * *